United States Patent [19]

Römer et al.

[11] Patent Number: 5,021,242
[45] Date of Patent: Jun. 4, 1991

[54] SOLID DRUG PREPARATIONS CONTAINING MICRONIZED CRYSTALS OF EBSELEN

[75] Inventors: Axel Römer, Hürth-Gleuel; Jürgen Seidel, Pulheim, both of Fed. Rep. of Germany

[73] Assignee: A. Nattermann & Cie GMBH, Cologne, Fed. Rep. of Germany

[21] Appl. No.: 209,325

[22] Filed: Jun. 20, 1988

[30] Foreign Application Priority Data

Jun. 20, 1987 [DE] Fed. Rep. of Germany ....... 3720493

[51] Int. Cl.$^5$ .............................................. A61K 9/02
[52] U.S. Cl. ..................... 424/436; 424/464; 424/465; 424/489; 424/490
[58] Field of Search ............... 424/489, 490, 464, 465, 424/436

[56] References Cited

U.S. PATENT DOCUMENTS

| | | | |
|---|---|---|---|
| 4,352,799 | 10/1982 | Renson et al. | 424/489 X |
| 4,711,961 | 12/1987 | Welter et al. | 544/182 X |
| 4,757,063 | 7/1988 | Parnham | 514/183 |
| 4,784,994 | 11/1988 | Romer et al. | 514/183 |

*Primary Examiner*—Thurman Page
*Attorney, Agent, or Firm*—Pearne, Gordon, McCoy & Granger

[57] ABSTRACT

The invention is related to solid drug preparations of 2-phenyl-1,2-benzisoselenazol-3(2H)-one (EBSELEN) with high bioavailability comprising EBSELEN in the form of micronized crystals, and a method of manufacturing the same.

2 Claims, 1 Drawing Sheet

Mean Plasma Concentrations
Micro and non-micro Ebselen 1000 mg

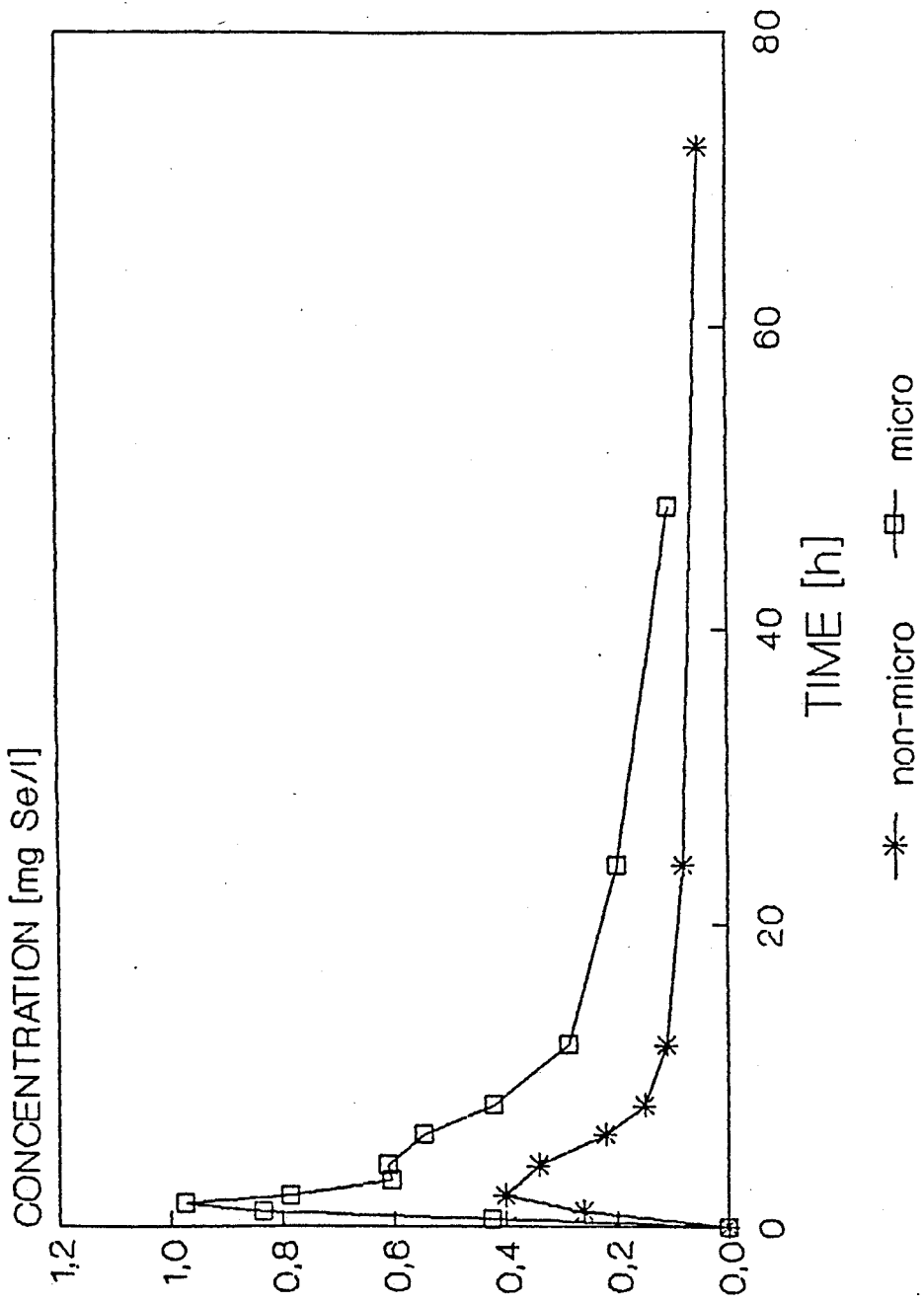

SOLID DRUG PREPARATIONS CONTAINING MICRONIZED CRYSTALS OF EBSELEN

The invention relates to solid drug preparations of 2-phenyl-1,2-benzisoselenazol-3(2H)-one (EBSELEN) with high bioavailability thereof and other valuable pharmacological properties, and a method of manufacturing them.

EBSELEN is a known substance (DE-PS 3027073) and can be produced by the method of R. Weber and M. Renson, Bulletin de la Soc. Chim. de France 1976 (7/8), 1124–1126, by reacting 2-methylseleno-N-phenyl benzamide with phosphorus pentachloride and subsequent hydrolysis. EBSELEN preparations can be used for treating numerous diseases, e.g. for prevention and treatment of infectious diseases, treatment of malignant tumours, and stimulating the immune system or in the case of selenium deficiency diseases. There are noteworthy anti-arteriosclerotic and anti-inflammatory properties for treatment of rheumatic diseases. In addition, EBSELEN is suitable for treating diseases caused by cell damage resulting from increased formation of active oxygen metabolites, e.g. liver injuries, cardiac infarct, psoriasis or injury through radiation. However, the wide range of action is offset by the low solubility of EBSELEN in water and the resulting reduction of biovailability.

It is an object of the present invention to provide solid drug preparations of EBSELEN which have an improved bioavailability.

The solid drugs preparation of EBSELEN according to the present invention are characterized in that they contain EBSELEN in micronized form with an EBSELEN average particle diameter of less than 10 μm, preferably between 10 and 0.5 μm.

The bioavailability mainly characterizes the amount of a drug which reaches the blood circulation after a drug form has been administered. Bioavailability is usually measured by using blood-level curves. This assumes that the drug or the corresponding metabolites are detectable in the blood by chemical analysis and that the blood level is related to the therapeutic efficacy of the drug.

A comparison was made between the areas under the blood (plasma) concentration-time curves (AUC=area under curve). The area under the curve corresponds to the amount of drug reaching the systemic circulation, depending on the distribution volume and the elimination rate constant (metabolism and excretion).

The bioavailability is characterized by using the following parameters:
 the area under the blood-level curve (AUC),
 the height of the blood-level maximum $C_{max}$, and
 the time for reaching the blood-level maximum $T_{max}$.

Blood tests on minipigs given equal doses showed that micronized EBSELEN produces a surprising increase in bioavailability.

Crystalline EBSELEN obtained by synthesis and having an average particle size of 70 μm—the substance previously used—was compared with micronized EBSELEN having an average particle size of <10 μm, in particular of 2 μm.

EBSELEN in micronized (2 μm) and crystalline (70 μm) form was administered in hard gelatine capsules in a dose of 50 mg/kg body weight to fasting minipigs.

The resulting plasma concentration curves against time are shown in FIG. 1 and, though similar in form, show very marked differences in the $C_{max}$ values and consequently also in the AUC values.

The micronized form gave a plasma level of 4.5 to 5.5 mg Se/l between one and four hours after ingestion. In the case of 70 μm EBSELEN the plasma concentration was appreciably lower, between 1.5 and 2.5 mg Se/l for a comparable $T_{max}$.

After 48 hours the plasma level returned to its original value in both cases.

The average AUC values (0–48 h) for the two formulations were:
 41 mg×h/l for the 70 μm form and
 61 mg×h/l for the 2 μm form.

The average cumulative excretion via the urine—as a percentage of the dose—during a 48-hour period was 28 for the 70 μm form and 59 for the maximal form.

As these results show, the new micronized form of EBSELEN has considerable advantages over the 70 μm form.

The average plasma level is increased by a factor of 2 and so is the excretion via the urine, and the AUC value is about 50% greater.

The new micronized form of EBSELEN has increased bioavailability and it can be used with greater prospects of success for treatment of numerous diseases, e.g. prevention and treatment of infectious diseases, stimulating the immune system, or in selenium deficiency diseases.

The new micronized form is particularly characterized by anti-arteriosclerotic and anti-inflammatory properties. It is therefore particularly suitable for treatment of rheumatic diseases such as arthroses or chronic polyarthritis, liver therapy, or treatment of skin diseases such as psoriasis. The new formulations are tolerated extremely well since they are non-toxic and, in contrast to known anti-inflammatory drugs, do not produce any ulcers or gastrointestinal irritation.

The invention also relates to a method of producing solid drug preparations of EBSELEN containing crystals thereof having an average diameter of <10 μm, in particular 0.5 to 10, such as 2 μm.

The EBSELEN crystals used according to the invention, having an average diameter of <10 μm, are produced by grinding crystals obtained in the synthesis of EBSELEN. Pinned disc mills or hammer mills can be used. EBSELEN with the desired particle size is obtained by varying the speed of the mill, the feed rate of product and/or the duration of grinding. It is particularly advantageous to use air-jet mills for grinding. The drug preparations according to the invention are produced by mixing or granulating micronized EBSELEN crystals with suitable adjuvants and producing solid drug preparations from the mixtures or granulates by conventional methods.

The following are examples of preferred drug preparations: tablets, pills, dragees and capsules.

The invention also relates to pharmaceutical preparations containing micronized EBSELEN. The pharmaceutical preparations according to the invention are for enteral, oral, rectal or parenteral application and contain the pharmaceutical active principle either alone or together with a conventional excipient in pharmaceutical use. Advantageously the pharmaceutical preparation of the active principle is in the form of individual doses adapted to the required method of administration, e.g. tablets, dragees, capsules, suppositories or granulates. The dosage of active principle is usually between 10 and 2000 mg per day, preferably between 30 and 300 mg per day, and can be administered in one dose or a number of partial doses, preferably two or three per day.

Manufacture of the drug preparations according to the invention is illustrated in detail by the following Examples.

EXAMPLE 1

| Tablet | |
| --- | --- |
| Micronized EBSELEN having an average diameter of 0.5 μm | 250 mg |
| Lactose | 160 mg |
| Kollidon 25 | 10 mg |
| Corn starch | 52 mg |
| Talcum | 12 mg |

The listed substances are mixed and pressed by conventional methods. The pressed articles can be film-coated if required.

EXAMPLE 2

| Capsule | |
| --- | --- |
| Micronized EBSELEN having an average diameter of 2 μm | 100 mg |
| Talcum | 10 mg |
| Aerosil 200 | 200 mg |

The listed substances are mixed and granulated by conventional methods and poured into hard gelatine capsules.

What we claim is:

1. Solid drug preparations of 2-phenyl-1,2-benzisoselenazol-3(2H)-one with high bioavailability thereof, characterized in that they contain 2-phenyl-1,2-benzisoselenazol-3(2H)-one in the form of micronized crystals having an average particle diameter from about 0.5 to about 2 μm, and said preparations are in the form of tablets, pills, dragees, capsules or suppositories.

2. A method of producing solid drug preparations of 2-phenyl-1,2-benzisoselenazol-3(2H)-one with high bioavailability thereof, characterized in that synthesized crystals of 2-phenyl-1,2-benzisoselenazol-3(2H)-one are micronized by grinding and/or screening into a crystal powder having an average particle diameter from about 0.5 to about 2 μm, and solid drug preparations in the form of tablets, pills, dragees, capsules or suppositories are formulated from the micronized crystals with admixtures of adjuvants and excipients.

* * * * *